United States Patent [19]

Knifton

[11] 4,339,545

[45] Jul. 13, 1982

[54] ALKANOLS FROM SYNTHESIS GAS

[75] Inventor: John F. Knifton, Austin, Tex.

[73] Assignee: Texaco Inc., White Plains, N.Y.

[21] Appl. No.: 277,540

[22] Filed: Jun. 26, 1981

[51] Int. Cl.$^3$ ............................................ C07C 27/06
[52] U.S. Cl. .................................. 518/700; 518/715;
    252/412; 252/428; 252/431 C
[58] Field of Search ................................ 518/700, 715

[56] References Cited

U.S. PATENT DOCUMENTS 4,042,614  8/1977  Vannice et al. .................... 518/715
4,265,828  5/1981  Knifton ............................... 518/700

*Primary Examiner*—Howard T. Mars
*Attorney, Agent, or Firm*—Carl G. Ries; Jack H. Park; Walter D. Hunter

[57] ABSTRACT

This invention concerns a process for making alkanols which comprises contacting a mixture of CO and $H_2$ at a pressure of 500 psig or greater and at a temperature of at least 150° C. with a catalyst system comprising a ruthenium-containing compound and a halogen-free titanium or zirconium-containing compound dispersed in a low melting quaternary phosphonium or ammonium base or salt.

24 Claims, No Drawings

ALKANOLS FROM SYNTHESIS GAS

BACKGROUND OF THE INVENTION

1. Field of the Invention

This invention concerns an improved process for preparing alkanols and especially ethanol by reaction of oxides of carbon with hydrogen in presence of a catalyst system.

2. Prior Art

It has long been known that monofunctional alcohols such as methanol, ethanol, etc. can be formed by the reaction of synthesis gas, i.e., a mixture of carbon monoxide and hydrogen at elevated pressures of, for example, up to 1000 atmospheres, and at temperatures of from about 200° to 500° C. or more using as a catalyst a mixture of copper, chromium and zinc oxides. A wide variety of other catalysts have been employed in the reaction of carbon monoxide and hydrogen to yield liquid products containing substantial amounts of monofunctional alcohols as exemplified by methanol, ethanol, propanol, etc. For example, in U.S. Pat. No. 4,013,700 the reaction of carbon monoxide and hydrogen in the presence of a quaternary phosphonium cation and a rhodium carbonyl complex yields a liquid product having a high methanol content. In U.S. Pat. No. 4,014,913 where the same reactants are contacted with a solid catalyst comprising a combination of rhodium and manganese the product formed contains substantial amounts of ethanol and in U.S. Pat. No. 4,197,253 where the reaction of carbon monoxide and hydrogen is conducted in the presence of a rhodium carbonyl complex and a phosphine oxide compound the resulting product contains a high concentration of methanol. Likewise, when the same reactants are contacted with a rhodium carbonyl complex and a copper salt a liquid product containing a substantial amount of methanol is formed.

One serious problem associated with synthesis gas operations in the past has been the non-selectivity of the product distribution since high activity catalysts generally yield a liquid product containing numerous hydrocarbon products and hydrocarbons as well. Thus, complicated recovery schemes are necessary to separate the desired products and the overall yield of the valuable organic products is low. This is a definite need in the art for a process which will produce alkanols and especially ethanol-rich alkanols with a high degree of selectivity from synthesis gas.

This invention therefore is to provide a process of making alkanols by resort to a unique catalyst system which produces said alkanols in good yields and with excellent selectivity especially with regard to ethanol formation.

SUMMARY OF THE INVENTION

This invention concerns a method for making alkanols rich in ethanol which comprises contacting a mixture of CO and $H_2$ at a pressure of 500 psig or greater and a temperature of at least 150° C. with a catalyst system comprising a ruthenium-containing compound and a halogen-free titanium or zirconium-containing compound dispersed in a low melting quaternary phosphonium or ammonium base or salt.

DETAILED DESCRIPTION OF THE INVENTION

In the narrower and more preferred practice of this invention, alkanols rich in ethanol are prepared by contacting a mixture of carbon monoxide and hydrogen at a temperature between about 180° and about 250° C. and at a pressure of 2000 psig or greater with a catalyst system comprised of a ruthenium-containing compound and a halogen-free titanium or zirconium-containing compound dispersed in a low melting quaternary phosphonium base or salt of an organic or mineral acid.

If desired, in practicing this invention, mixutres of the ruthenium-containing compounds as well as the titanium or zirconium-containing compounds may be employed.

Catalysts that are suitable in the practice of this invention contain ruthenium and titanium or zirconium. The catalysts may be chosen from a wide variety of organic or inorganic compounds, complexes, etc., as will be shown and illustrated below. It is only necessary that the catalyst precursor actually employed contain said metals in any of their ionic states. The actual catalytically active species is then believed to comprise ruthenium and titanium or zirconium in complex combination with carbon monoxide and hydrogen. The most effective catalysis is believed to be achieved where ruthenium and titanium or zirconium hydrocarbonyl species are solubilized in a quaternary salt under reaction conditions.

The ruthenium catalyst precursors may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) triiodide, tricarbonyl ruthenium(II) iodide, anhydrous ruthenium(III) chloride and ruthenium nitrate, or as the salt of a suitable organic carboxylic acid, for example, ruthenium(III) acetate, ruthenium napththenate, ruthenium valerate and ruthenium complexes with carbonyl-containing ligands, such as ruthenium(III) acetylacetonate. The ruthenium may also be added to the reaction zone as a carbonyl or hydrocarbonyl derivative. Here, suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Ruthenium complexes containing Group VB Donor ligands such as triphenylphosphine may be effective catalyst precursors under certain conditions.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The titanium and zirconium catalyst precursors may take many different forms. For instance, the titanium or zirconium may be added to the reaction mixture in an oxide form, as in the case of, for example, of titanium(II) oxide, titanium(III) oxide, titanium(IV) oxide and zirconium oxide ($Zr_2O_3$). Alternatively, it may be added as the halogen-free salt of a mineral acid, as in the case of titanium nitrate and zirconium sulfate, oxide [$ZrO(SO_4)\cdot H_2SO_4 3H_2O$], as the salt of a suitable organic carboxylic acid, for example, titanium acetate, zirconium- (IV) acetate, zirconium diacetate oxide, zirconyl acetate, titanium(IV) nonylate and titanium stearylate, as a titanium or zirconium alkoxide, as in the case of titanium(IV) methoxide, titanium(IV) ethoxide, titanium(IV) 2-ethylmethoxide, titanium(IV) i-propoxide, and zirconium n-propoxide, or as a titanium or zirconium hydride, for example, titanium(II) hydride and zirconium hydride. The titanium or zirconium may also be introduced as a complex with a carbonyl-containing ligand, as in the case of titanium acetylacetonate, or as a mixed ligand complex as in the case of titanium(IV) butoxybis-(2,4-pentanedionate), $(C_4H_9O)_2Ti(C_5H_7O_2)_2$ or titanium (di-i-propoxide) bis(2,4-pentanedionate). Titanium and zirconium carbide, carbonyl or hydrocarbonyl derivatives, such as titanium(IV) carbide and zirconium carbide, are also effective catalyst precursors.

Preferred titanium and zirconium-containing compounds include salts of organic acids such as zirconium-(IV) acetate, zirconium diacetate oxide, $(ZrO(OAc)_2 \cdot H_2O)$, and zirconyl acetate, $(H_2ZrO_2(OAc)_2)$, titanium acetate, titanium and zirconium complexes or carbonyl-containing ligands such as titanium(III) acetylacetonate and zirconium(IV) acetylacetonate, titanium and zirconium alkoxides such as titanium(IV) methoxide and zirconium(IV) methoxide, as well as mixed ligand complexes such as titanium(IV) butoxybis(2,4-pentanedionate).

The ruthenium-containing compound and the halogen-free titanium or zirconium-containing compound are prior to their catalytic use in making alkanols, first dispersed in a low melting quaternary phosphonium or ammonium base or salt. It is interesting to note that the ruthenium-containing compound alone, without being dispersed in said salt or base, has little, if any activity in promoting the manufacture of alkanols for synthesis gas.

The quaternary phosphonium or ammonium base or salt must be relatively low melting, that is, melt at a temperature less than about the temperature of reaction of making alkanols. Usually the quaternary compound has a melting point less than about 180° C. and most often has a melting point less than 150° C.

Suitable quaternary phosphonium salts have the formula:

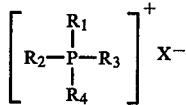

where $R_1$, $R_2$, $R_3$ and $R_4$ are organic radicals, particularly aryl or alkaryl radicals bonded to the phosphorous atom, and X is an anionic species. The organic radicals useful in this instance include those alkyl radicals having 1 to 20 carbon atoms in a branched or linear alkyl chain; they include the methyl, ethyl, n-butyl, iso -butyl, octyl, 2-ethylhexyl and dodecyl radicals. Tetraethylphosphonium bromide and tetrabutylphosphonium bromide are typical examples presently in commercial production. The corresponding quaternary phosphonium acetates, hydroxides, nitrates, chromates, tetrafluoroborates and other halides, such as the corresponding chlorides, and iodides, are also satisfactory in this instance. Also useful are the corresponding quaternary ammonium bases and salts in the above series of compounds.

Equally useful are the phosphonium and ammonium salts containing phosphorus or nitrogen bonded to a mixture of alkyl, aryl and alkaryl radicals. Said aryl and alkaryl radicals may each contain 6 to 20 carbon atoms. The aryl radicals may each contain 6 to 20 carbon atoms. The aryl radical is most commonly phenyl. The alkaryl group may comprise phenyl substituted with one or more $C_1$-$C_{10}$ alkyl substituents, bonded to the phosphorus or nitrogen atom through the aryl function.

Illustrative examples of suitable quaternary phosphonium and ammonium bases and salts include tetrabutylphosphonium bromide, heptyltriphenylphosphonium bromide, tetrabutylphosphonium iodide, tetrabutylphosphonium chloride, tetrabutylphosphonium nitrate, tetrabutylphosphonium hydroxide, tetrabutylphosphonium chromate, tetrabutylphosphonium tetrafluoroborate, tetrabutylphosphonium acetate, tetrabutylammonium bromide and tetramethylammonium hydroxide, pentahydrate and trimethyldodecylammonium bromide.

The preferred quaternary salts are generally the tetralkylphosphonium salts containing alkyl groups having 1-6 carbon atoms, such as methyl, ethyl, and butyl. Tetrabutylphosphonium salts, such as tetrabutylphosphonium bromide, are most preferred for the practice of this invention. Preferred tetrabutylphosphonium salts or bases include the bromide, chloride, iodide, acetate and chromate salts and hydroxide base.

Generally, in the catalyst system the molar ratio of the ruthenium compound to the quaternary phosphonium or ammonium salt or base will range from about 1:0.01 to about 1:100 or more and, preferably, will be from about 1:0.5 to about 1:20.

The quantity of ruthenium compound employed in the instant invention is not critical and may vary over a wide range. In general, the novel process is desirably conducted in the presence of a catalytically effective quantity of the active ruthenium species and of the titanium or zirconium which gives the desired product in reasonable yield. The reaction proceeds when employing as little as about $1 \times 10^{-6}$ weight percent, and even lesser amounts, of ruthenium together with about $1 \times 10^{-6}$ weight percent or less of titanium or zirconium, basis the total weight of the reaction mixture. The upper concentration is dictated by a variety of factors including catalyst cost, partial pressures of carbon monoxide and hydrogen, operating temperature, etc. A ruthenium concentration of from about $1 \times 10^{-5}$ to about 5 weight percent in conjunction with a titanium or zirconium concentration of from about $1 \times 10^{-5}$ to about 5 weight percent, based on the total weight of reaction mixture is generally desirable in the practice of this invention.

The temperature range which can usefully be employed in these synthesis is a variable dependent upon other experimental factors, including the pressure, and the concentration and choice of the particular species of the ruthenium catalyst as well as the titanium or zirconium co-catalyst among other things. The range of operability is from about 150° to 350° C. when superatmospheric pressure of syngas are employed. A narrow range of 180°–250° C. represents the preferred temperature range.

Superatmospheric pressures of 500 psig or greater lead to substantial yields of alkanols by the process of this invention. A preferred operating range is from 2000 psig to 9000 psig, although pressures above 9000 psig also provide useful yields of the desired alkanols.

The relative amounts of carbon monoxide and hydrogen which may be initially present in the syngas mixture are variable, and these amounts may be varied over a wide range. In general, the mole ratio of $CO:H_2$ is in the range from about 20:1 up to about 1:20, preferable from about 5:1 to 1:5, although ratios outside these ranges may also be employed. Particularly in continuous operations, but also in batch experiments, the carbon monoxide-hydrogen gaseous mixtures may also be used in conjunction with up to 50 percent by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Ester of monocarboxylic acids may also be formed during the course of this desired alkanol synthesis. Most often these derivatives are esters of acetic acid such as methyl acetate, ethyl acetate, propyl acetate, etc. These esters and the individual alcohols formed can be conveniently recovered from the reaction mixture by distillation extraction, etc.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired alkanols and said material may be recovered, as previously pointed out, by methods well known in the art, such as distillation, fractionation, extraction and the like. A fraction rich in the catalyst components may then be recycled to the reaction zone, if desired, and additional products generated.

The products have been identified in this work by one or more of the following analytical procedures, viz, gas-liquid phase chromatograph (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

The following examples illustrate various embodiments of this invention and are to be considered not limitative.

EXAMPLE 1

This example illustrates the synthesis of an ethanol-rich alkanol ester mixture directly from synthesis gas using a titanium-ruthenium containing catalyst dispersed in tetrabutylphosphonium bromide salt (m.p. 100° C.).

A mixture of ruthenium (IV) oxide, hydrate (4 mmoles) and titanium acetylacetonate dibutoxide (4 mmoles) dispersed in tetrabutylphosphonium bromide (10.0 g, 29.7 mmole) was transferred in a glass liner under nitrogen purge, to an 850 ml capacity pressure reactor equipped with heating and means of agitation. The reactor was sealed, flushed with a mixture of carbon monoxide and hydrogen and pressured to 2000 psig with the carbon monoxide-hydrogen mixture (1:1 molar). The mixture was heated to 220° C. with rocking, the pressure raised to 4000 psig by addition of the carbon-monoxide-hydrogen mixture from a large surge tank, and the reactor held at temperature for 18 hours. Pressure was maintained in the reactor at circa 4000 psig by incremental additions of the carbon monoxide-hydrogen mixture from the surge tank.

On cooling, the reactor pressure (1795 psig) was noted, a typical gas sample taken, and the excess gas removed. The dark-brown liquid product (33.1 g) was analyzed by gas liquid chromatography and Karl-Fischer titration and the following results were obtained:

| | |
|---|---|
| 40.7 wt. % ethanol | 3.5 wt. % methyl acetate |
| 16.3 wt. % methanol | 8.0 wt. % ethyl acetate + methyl propionate |
| 4.3 wt. % n-propanol | 4.3 wt. % propyl acetate + ethyl propionate |
| 4.1 wt. % n-butanol | 2.0 wt. % water |

The liquid yield increase was: $(33.1-12.3)/12.2 \times 100 = 169$ wt.%. Here $C_1$–$C_4$ alkanols constituted 65% of the liquid product and ethanol comprised 62% of the alkanol fraction.

The alkanol and ester product fractions were recovered from the crude liquid product by fractional distillation in vacuo. Distillate fractions showed high alcohol content. The dark-brown liquid residue (11.0 g) resolidified upon cooling.

Analyses of typical off-gas samples show the presence of:

| | |
|---|---|
| 30% hydrogen | 36% carbon dioxide |
| 20% carbon monoxide | 9% methane |

EXAMPLES 2–7

A number of additional examples utilizing ruthenium and titanium-containing catalysts were conducted in the same manner as described in Example 1.

Here combination of ruthenium(IV) oxide and ruthenium(III) acetylacetonate with titanium(III) acetylacetonate, titanium(IV) methoxide and a mixed alkoxide, acetylacetonate titanium complexe, titanium butoxy bis(2,4-pentanedionate), when dispersed in tetrabutylphosphonium bromide and tetrabutyphosphonium iodide, were shown to be effective for syngas conversion to ethanol-rich alkanol mixtures. The results for these examples are set out in Table I which follows.

TABLE I[a]

EXAMPLES 1–7

| Run | Catalyst | Melt | Max. Press. | °C. Temp. | LIQUID COMPOSITION (WT. %) Alcohols | | | |
|---|---|---|---|---|---|---|---|---|
| | | | | | MeOH | EtOH | PrOH | BuOH |
| 1 | $RuO_2$—Ti(acac)$_2$(OBu)$_2$ | Bu$_4$PBr | 6285 | 220 | 16.3 | 40.7 | 4.3 | 4.1 |
| 2 | $RuO_2$—Ti(OMe)$_4$ | Bu$_4$PBr | 6250 | 220 | 21.0 | 39.0 | 5.4 | 5.6 |
| 3 | $RuO_2$—Ti(acac)$_3$ | Bu$_4$PBr | 6365 | 220 | 15.0 | 27.6 | 3.2 | 3.7 |
| 4 | $RuO_2$—Ti(acac)$_3$ | Bu$_4$PBr | 6330 | 220 | 19.3 | 38.6 | 4.2 | 2.6 |
| 5 | $RuO_2$—Ti(acac)$_2$(OBu)$_2$ | Bu$_4$PI | 6300 | 220 | 16.2 | 34.9 | 5.0 | 5.5 |

TABLE I[a] -continued

EXAMPLES 1-7

| | | | Max. Press. | °C. Temp. | | | | |
|---|---|---|---|---|---|---|---|---|
| 6 | RuO$_2$—Ti(acac)$_2$(OBu)$_2$ | Bu$_4$PBr | 5000[b] | 220 | 8.4 | 5.2 | 0.8 | 2.4 |
| 7 | Ru(acac)$_3$—Ti(acac)$_2$(OBu)$_2$ | Bu$_4$PBr | 6565[c] | 220 | 20.4 | 33.0 | 3.2 | 2.1 |

| | LIQUID COMPOSITION (WT. %) | | | | | |
|---|---|---|---|---|---|---|
| | | Esters | | | | |
| Run | MeOAc | EtOAc/ MeOOPr | PrOAc/ EtOOPr | H$_2$O | Liquid Yields % |
| 1 | 3.5 | 8.0 | 4.3 | 2.0 | 169 |
| 2 | 3.6 | 6.1 | 3.1 | 2.0 | 239 |
| 3 | 2.6 | 3.7 | 0.3 | 10.4 | 253 |
| 4 | 3.9 | 6.4 | 0.5 | — | 230 |
| 5 | 2.1 | 3.7 | 1.5 | 1.9 | 33 |
| 6 | 0.3 | 1.0 | 0.2 | 76.5 | 120 |
| 7 | 6.1 | 8.1 | 3.3 | 3.0 | 214 |

[a] Run conditions as outlined in Example 1.
[b] Run with 1:2 CO/H$_2$ constant pressure run.
[c] Run for 10 hours at temp.

EXAMPLES 8-10

The use of zirconium-ruthenium-containing catalysts is illustrated in Examples 8-10 which were carried out using the same general procedure as employed in Example 1.

Here, combinations of ruthenium(IV) oxide with zirconium(IV) acetylacetonate, zirconium acetate and zirconyl acetate, when dispersed in tetrabutylphosphonium bromide were shown to be effective for syngas conversion to ethanol-rich alkanol mixtures. The results for these examples are set out in Table II which follows.

On cooling the excess gas was removed. An orange solid (11.1 g) was recovered from the reactor. There was no liquid product.

What is claimed is:

1. A process for making alkanols which comprises contacting a mixture of CO and H$_2$ at a pressure of 500 psig or greater and at a temperature of at least 180° C. with a catalyst system comprising a ruthenium-containing compound and a material selected from the group consisting of a halogen-free titanium-containing compound and a halogen-free zirconium-containing compound dispersed in a low melting quaternary phosphonium or ammonium base or salt.

TABLE II[a]

EXAMPLES 8-10

| | | | | | LIQUID COMPOSITION (WT. %) | | | |
|---|---|---|---|---|---|---|---|---|
| | | | | | Alcohols | | | |
| Run | Catalyst | Melt | Max. Press. | °C. Temp. | MeOH | EtOH | PrOH | BuOH |
| 8 | RuO$_2$—Zr(acac)$_4$ | Bu$_4$PBr | 6300 | 220 | 8.0 | 28.5 | 4.3 | 3.8 |
| 9 | RuO$_2$—Zr(OAc)$_4$ | Bu$_4$PBr | 6300 | 220 | 4.1 | 11.9 | 1.7 | 1.8 |
| 10 | RuO$_2$—H$_2$ZrO$_2$(OAc)$_2$ | Bu$_4$PBr | 6350 | 220 | 24.6 | 24.7 | 2.6 | 6.4 |

| | LIQUID COMPOSITION (WT. %) | | | | |
|---|---|---|---|---|---|
| | | Esters | | | |
| Run | MeOAc | EtOAc/ MeOOPr | PrOAc/ EtOOPr | H$_2$O | Liquid Yields % |
| 8 | 1.3 | 7.5 | 1.9 | 12.0 | 156 |
| 9 | 1.4 | 6.4 | 0.8 | 26.1 | 225[b] |
| 10 | 1.9 | 1.1 | 2.1 | 9.8 | 230 |

[a] Run condition as outlined in Example 1.
[b] Liquid product sample consists of two phases: 75% is the alcohol/ester mix shown here and the remainder is a lighter, hydrocarbon-rich phase.

COMPARATIVE EXAMPLE 11

This example illustrates the inactivity of the titanium catalysts alone, in the absence of a ruthenium-containing component.

A mixture of titanium(IV) tetramethoxide (4.0 mmoles) dispersed in tetrabutylphosphonium bromide (10.0 g, 29.7 mmole) was transferred in a glass liner under nitrogen purge, to an 850 ml capacity pressure reactor. The reactor was sealed, flushed with a mixture of carbon monoxide and hydrogen and pressured to 2000 psig with the carbon monoxide-hydrogen mixture (1:1 molar). The mixture was heated to 220° C., the pressure raised to 6300 psig by addition of CO/H$_2$ mixture from a large surge tank, and the reactor held at temperature for 18 hours.

2. The process of claim 1 wherein the process is conducted at a pressure of about 200 psig to about 9000 psig.

3. The process of claim 1 wherein the process is conducted at a temperature of about 180° to about 250° C.

4. The process of claim 1 wherein the said material is a titanium-containing compound.

5. The process of claim 1 wherein the said material is a zirconium-containing compound.

6. The process of claim 1 wherein said quaternary salt or base has a melting point less than about 180° C.

7. The process of claim 1 wherein said quaternary salt is a tetraalkylphosphonium salt.

8. The process of claim 7 wherein said alkyl groups contain 1-6 carbon atoms.

9. The process of claim 1 wherein said quaternary is a mixed alkylaryl phosphonium quaternary.

10. The process of claim 1 wherein said quaternary salt is tetrabutylphosphonium salt.

11. The process of claim 10 wherein said tetrabutylphosphonium salt is selected from the group consisting of tetrabutylphosphonium bromide, tetrabutylphosphonium chloride, tetrabutylphosphonium iodide, tetrabutylphosphonium acetate and tetrabutylphosphonium chromate.

12. The process of claim 1 wherein said quaternary phosphonium base is tetrabutylphosphonium hydroxide.

13. The process of claim 1 wherein the ruthenium-containing compound is selected from the group consisting of one or more oxides of ruthenium, ruthenium salts of a mineral acid, ruthenium salts of an organic carboxylic acid and ruthenium carbonyl or hydrocarbonyl derivatives.

14. The process of claim 1 wherein the ruthenium-containing compound is selected from the group consisting of anhydrous ruthenium(IV) dioxide, ruthenium(IV) dioxide hydrate, ruthenium(VIII) tetraoxide, ruthenium(III) trichloride hydrate, ruthenium acetate, ruthenium propionate, ruthenium(III) acetylacetonate and triruthenium dodecarbonyl.

15. The process of claim 1 wherein said ruthenium-containing compound is ruthenium(IV) dioxide.

16. The process of claim 1 wherein said ruthenium-containing compound is ruthenium(III) acetylacetonate.

17. The process of claim 1 wherein the said material is a halogen-free titanium-containing compound selected from the group consisting of titanium salts of organic acids, titanium complexes of carbonyl-containing ligands and titanium alkoxides as well as mixed ligand complexes thereof.

18. The process of claim 1 wherein the titanium-containing compound is selected from the group consisting of titanium acetate, titanium(III) acetylacetonate, titanium(IV) methoxide, titanium(IV) ethoxide and titanium(IV) butoxybis(2,4-pentanedionate).

19. The process of claim 1 wherein said titanium containing compound is titanium acetylacetonate.

20. The process of claim 1 wherein said titanium containing compound is titanium(IV) methoxide.

21. The process of claim 1 wherein the said material is a halogen-free zirconium-containing compound selected from the group consisting of zirconium salts of organic acids, zirconium complexes of carbonyl-containing ligands, zirconium alkoxides and zirconyl compounds as well as mixed ligand complexes thereof.

22. The process of claim 1 wherein the zirconium-containing compound is selected from the group consisting of zirconium(IV) acetate, zirconyl acetate, zirconium diacetate oxide, zirconium methoxide, and zirconium(IV) acetylacetonate.

23. The process of claim 1 wherein said zirconium-containing compound is zirconium(IV) acetate.

24. The process of claim 1 wherein said zirconium-containing compound is zirconium(IV) acetylacetonate.

* * * * *